United States Patent [19]
Swain et al.

[11] Patent Number: 5,448,608
[45] Date of Patent: Sep. 5, 1995

[54] TOMOGRAPHIC SCANNER HAVING CENTER OF ROTATION FOR ALL PHYSICS

[75] Inventors: Ronald E. Swain, Reading; Gilbert W. McKenna, Revere, both of Mass.

[73] Assignee: Analogic Corporation, Peabody, Mass.

[21] Appl. No.: 351,880

[22] Filed: Dec. 8, 1994

Related U.S. Application Data

[63] Continuation of Ser. No. 193,696, Feb. 8, 1994, abandoned.

[51] Int. Cl.⁶ .................................................. A61B 6/00
[52] U.S. Cl. ................................................ 378/4; 378/15; 378/20
[58] Field of Search ................. 378/4, 15, 19, 20, 193, 378/197, 198, 204

[56] References Cited

U.S. PATENT DOCUMENTS

| | | | |
|---|---|---|---|
| 4,093,863 | 6/1978 | Zacher, Jr. | 378/4 |
| 4,200,797 | 4/1980 | Bax | 378/15 |
| 4,928,283 | 5/1990 | Gordon . | |
| 4,995,069 | 2/1991 | Tanaka | 378/200 |

FOREIGN PATENT DOCUMENTS 2026812  2/1980  United Kingdom ................ 378/15

*Primary Examiner*—David P. Porta
*Attorney, Agent, or Firm*—Lappin & Kusmer

[57] ABSTRACT

A light-weight, portable X-ray tomography system having an annular frame supporting therein a concentric apertured drum rotatable in its plane about a rotational axis, and a plurality of components for performing a tomographic scan all mounted on the drum with respect to both sides of the mean plane of the drum so as to be dynamically balanced for rotation with the drum about the rotational axis, and so that the center of the mass moment of inertia, the center of rotation, the center of thermal expansion of the drum and components mounted thereon, and the center of the scanning plane substantially coincident on that rotational axis.

13 Claims, 3 Drawing Sheets

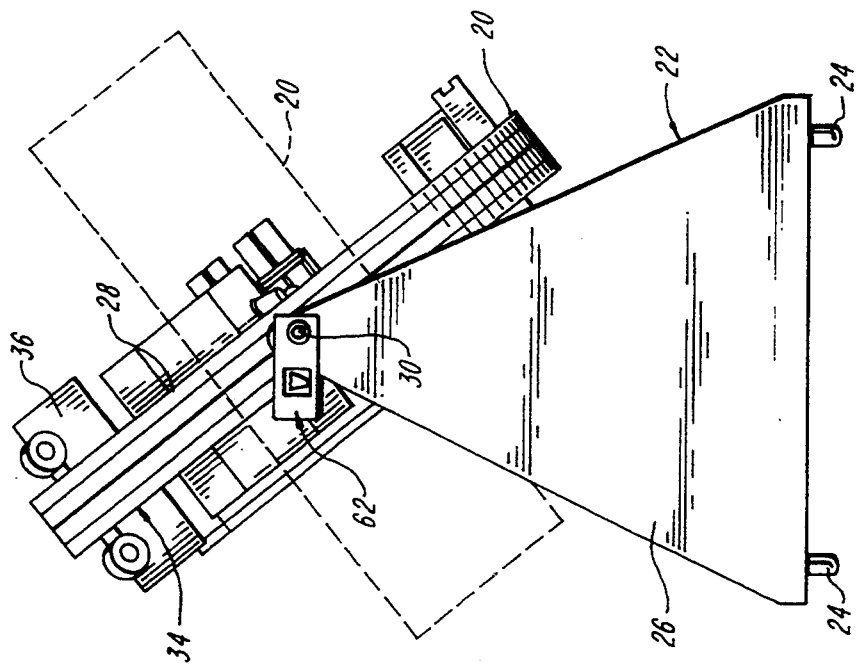
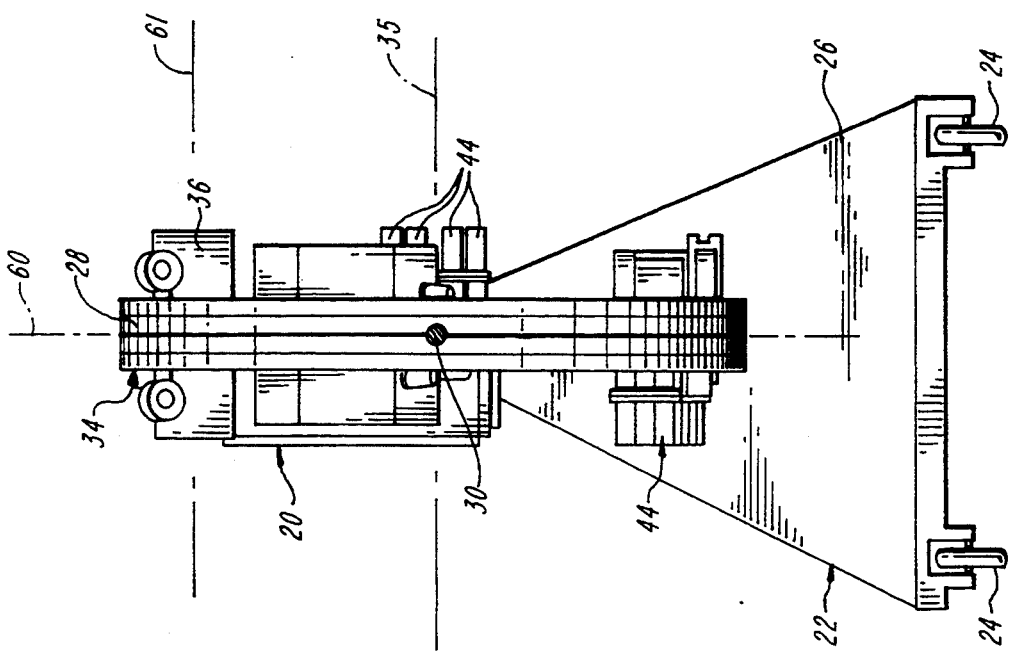

TOMOGRAPHIC SCANNER HAVING CENTER OF ROTATION FOR ALL PHYSICS

This is a continuation of application Ser. No. 08/193,696 filed on Feb. 8, 1994 now abandoned.

RELATED APPLICATIONS

This application is related to U.S. patent application Ser. No. 08/193,783, filed in the names of Gilbert W. McKenna and entitled "X-ray Tomographic Scanning System" (Attorney's Docket No. ANA-30); U.S. patent application Ser. No. 08/193,562, filed in the name of Gilbert W. McKenna and entitled "X-ray Tomography System with Gantry Pivot and Translation Control" (Attorney's Docket No. ANA-37); and U.S. patent application Ser. No. 08/193,782, filed in the name of Gilbert W. McKenna and entitled "Stabilized, Cantilevered Patient Trauma Table System" (Attorney's Docket No. ANA-58); all filed simultaneously herewith and assigned to the present assignee.

1. Field of the Invention

The present invention relates generally to X-ray tomographic apparatus, and more particularly to portable computerized axial tomography (CAT) scan systems.

2. Background of the Invention

Current CAT scan systems usually comprise a gantry formed of a structure such as a disk or drum rotatable within a frame held in a yoke, an X-ray source and an X-ray detector system. In both third and fourth generation systems, the X-ray source is mounted on the drum for rotational motion about a table on which a patient can repose. The X-ray source may provide periodic pulses or continuous wave radiation. In third generation machines the detector system includes an array of detectors mounted on the drum diametrically opposite the source and rotatable with the source. In fourth generation machines, the detectors are fixedly mounted on the gantry frame. In both types of systems, each detector is typically either a solid state or gas tube device, and is aligned with the source so that the detector X-ray input and the focal spot of the source are positioned within a common mean, scanning or rotation plane (normal to the axis of rotation of the drum). In the case of third generation machines, each detector of the array is positioned in the scanning plane at a predetermined angular spacing relative to the source so that each detector subtends an equal angle about the focal spot of the X-ray source, thus providing a plurality of different X-ray paths in the scanning plane between the source and the respective detectors for each projection view. In fourth generation machines a plurality of different X-ray paths are provided between each stationary detector and the moving source. The X-ray paths can collectively resemble a fan in third generation machines and fans in fourth generation machines, and consequently such systems are sometimes called "fan beam" tomography systems. During a scan the detectors respectively provide a plurality of information or data signals corresponding to variations in the radiation flux measured by the detectors during rotation of the drum about an object occupying the space between the detectors and the X-ray source. Upon known (Radon) mathematical processing of the signals, a visual image can be reconstructed representing the density distribution of a two-dimensional slice along the scanning plane, through the portion of any object positioned in the plane between the source and the detectors. The formation of such images critically depends upon the components remaining perfectly mechanically aligned within the scanning plane, particularly during rotation of the drum, and that the drum rotating about a precise axis of rotation.

Because during a scan even minor misalignment of the X-ray source and detector system of a CAT scan apparatus can result in faulty or erroneous images, such apparatus has been provided as massively reinforced devices often weighing a ton or more so as to prevent improper movement of the source and the detector system. Typically, all of the components are mounted on the drum with little regard to the weight distribution, with large counter weights added to one or both sides of the drum to insure that the drum will be balanced during rotation to prevent undesirable vibration. Such counter weights merely add to the overall weight and power requirements of the system. Further, such apparatus has large peak power requirements, typically on the order of many thousands of watts, and is usually tied directly to a source of line power fed to the X-ray source through slip-rings between the drum and the frame. Accordingly, the gantry is usually installed at a fixed location in a health facility, and the patients are brought to the apparatus for examination. In order to extend the examination to multiple locations along the patient's bodies, a patient table is usually provided in moveable form to permit positioning of the patient relative to the fixed frame.

Many of the disadvantages inherent in such a massive, expensive, relatively fixed CAT scan structure characteristic of the prior art have been recognized and addressed, at least in part, by the apparatus described and claimed in U.S. Pat. No. 4,928,283 issued May 22, 1990 to B. M. Gordon.

As described in the aforesaid U.S. Pat. No. 4,928,283, major components of the tomography apparatus, such as an X-ray source, a detector array in the case of third generation machines, an X-ray power source including a power converter and batteries, a power source for the detector array in the case of third generation machines, and a control and data handling electronics package, are all mounted on the rotatable drum. Accordingly, the term "components" as used herein can include not only one or more of these major components, but also any number of elements supported by the rotatable drum, depending upon the particular design of the tomographic scanner. For example, a number of minor components in the sense of mass and volume, such as a slice collimator, a motor driven fan for cooling the X-ray source, antiscatter plates for the detector array, a detector assembly control panel and/or the like are also typically mounted on the drum, and thus can be included in the term "components" as used herein. These latter components, however, will not necessarily be specifically mentioned hereinafter, the emphasis being placed on the heavier and bulkier components for the sake of brevity.

Where one desires to provide a CAT scan system that can be transported readily in and out of, for example, operating theaters and the like, it is desirable that the volume and weight of a gantry are minimized without jeopardizing the precision at which the system can accurately scan a patient during drum rotation. As a consequence, adding counter weights should be minimized. Further, it has now been realized that thermal expansion and contraction of the drum (due to the heat generated by the X-ray source and subsequent cooling after its use) tends to be non-linear, and particularly where some of the tomography components are mounted relatively randomly on the drum, the operation of the system can be adversely affected by temperature changes. Of course, other factors contributing to deviation of the fan beam from a predetermined plane during rotation of the drum can also adversely affect the system operation.

OBJECTS OF THE INVENTION

Accordingly it is a primary object of the present invention to provide an improved CAT scan system that overcomes the problems inherent in the massive, heavy and poorly mobile prior art systems.

Another object of the present invention is to provide such an improved tomography system that includes a rotatable drum in which the volume and weight are minimized without jeopardizing the precision at which the system accurately scans during drum rotation.

Other objects of the present invention will in part be obvious and will in part appear hereinafter. The invention accordingly comprises the apparatus possessing the construction, combination of elements and arrangement of parts which are exemplified in the following detailed disclosure and the scope of the application of which will be indicated in the claims.

SUMMARY OF THE INVENTION

The objects of the present invention are effected generally by the provision of an improved X-ray tomography structure in which the tomography components are mounted on an annulus. The annulus is provided with a central opening so as to form a thin, substantially planar drum mounted for rotation in its mean plane about a central rotation axis. The central opening is of sufficient dimensions for receiving the object to be scanned so as to allow X-rays from the source mounted on the drum to (a) pass through an object extending through the opening and (b) be detected by the detectors while the drum rotates in a circle about the object within which data is collected so that an image can be subsequently reconstructed from the data. The term "annulus" as used herein is intended to mean any substantially flat, radially symmetrical, centrally-apertured structure such as a drum, disk or ring, and hence includes but is not to be limited to flat or circular configurations.

Minimum size of the gantry is achieved by utilizing the center of the circle as the absolute center of rotation of the annulus, with the mean plane of the annulus being relatively close to, and preferably coplanar with the scanning plane defined by the fan beam of X-rays. The tomography components are fixedly mounted with respect to both of the opposite surfaces of the annulus so as to be balanced for rotation with the annulus about the center of rotation. Specifically, the center of mass, the center of rotation and the center of thermal expansion of the annulus and attached components are all coincident at the center of rotation of the drum within the mean plane of the annulus, and so that the axis of the moment of inertia of mass (i.e. the rotational inertia of the drum and attached components), is coaxial with the rotation axis.

BRIEF DESCRIPTION OF THE DRAWINGS

For a fuller understanding of the nature and objects of the present invention, reference should be had to the following detailed description taken in connection with the accompanying drawings wherein:

FIG. 3 is a cross-section taken along the line 3—3 of the embodiment of FIG. 2; and FIG. 4 is a schematic end view of the structure of FIGS. 1-3 showing the emplacement of load measuring apparatus to the pivot of a rotatable member in FIG. 1 and the positioning of that member for testing.

DETAILED DESCRIPTION OF THE DRAWINGS

Figure 1:
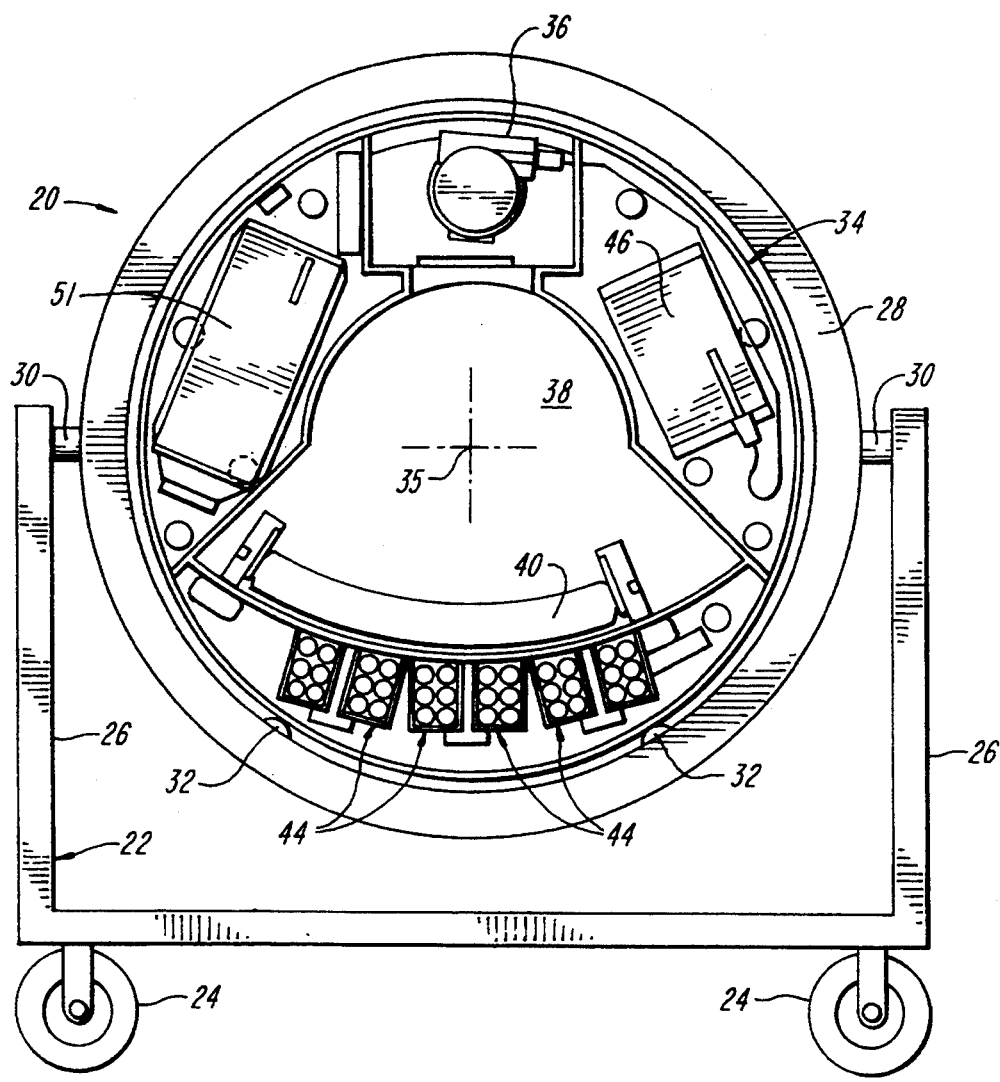
FIG. 1 is a from view of structure illustrating a CAT scanner of the third generation type and constructed according to the principles of the present invention.

In the drawings the same numerals are used to refer to similar or the same parts.

Figure 2:
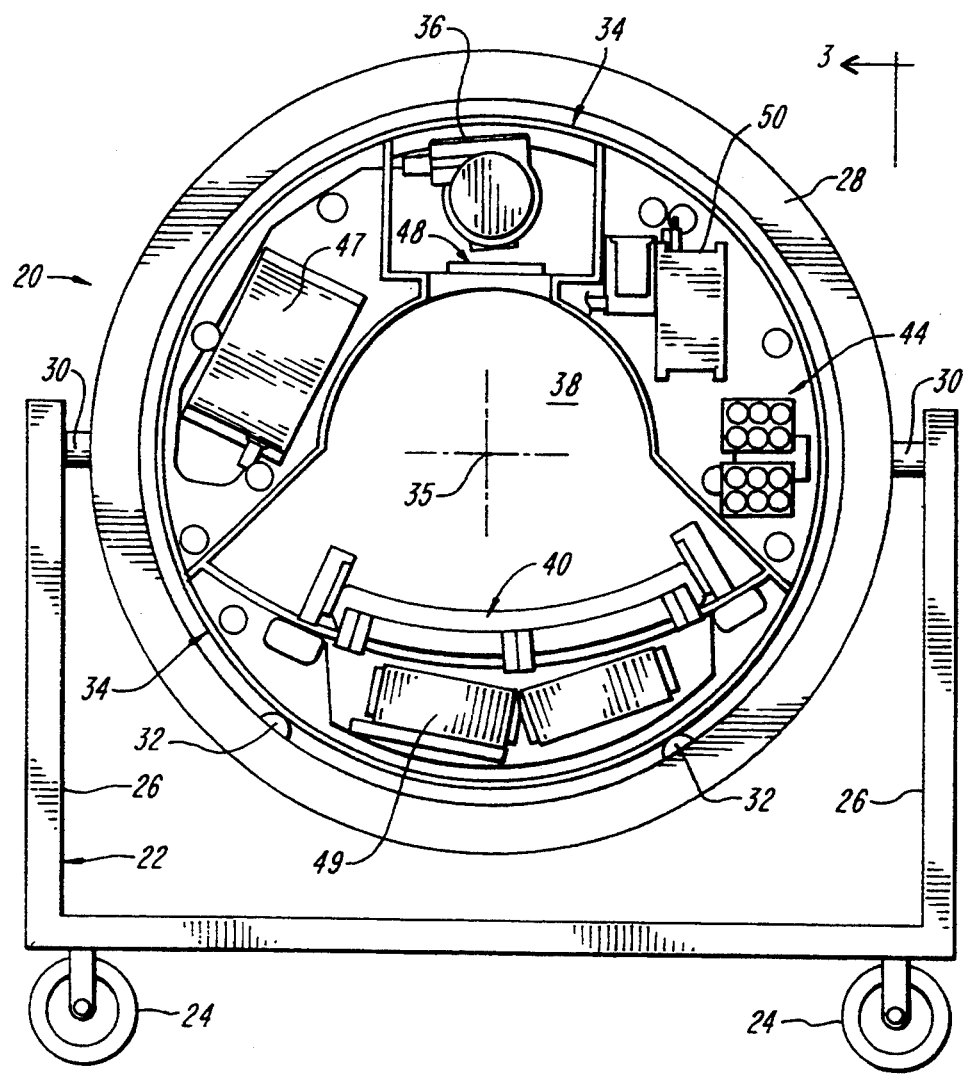
FIG. 2 is a rear view of the structure of FIG. 1.

Referring to FIGS. 1-3, there is shown a CAT scanner comprising a yoke or cart 22 for supporting a gantry 20 incorporating the principles of the present invention. Cart 22 is mounted on a plurality of wheels 24 so as to be movable or portable. Cart 22 comprises a pair of preferably rigid upright sides 26 between which is mounted the gantry 20. Gantry 20 includes a frame 28, typically formed as a metallic annulus or annular portion preferably made of a light-weight, rigid material such as aluminum, magnesium-aluminum alloy and the like, and can be solid or hollow to minimize weight. Preferably, frame 28 has a substantially uniform cross-sectional configuration and mass throughout, at least the inner periphery of frame 28 being circular. Frame 28 is pivotally mounted on cart 22 so that the gantry 20 can be tilted about a center line or diametrical axis defined by a pair of pivots 30. Each of pivots 30 is preferably fixed to frame 28 for movement therewith and extends into a corresponding bearing surface suitably supported by a respective one of sides 26 so that the gantry can be pivoted about pivots 30 and can be moved in translation backward and forward along sides 26. Frame 28 is restrained from rotation in its own plane by the coupling between pivots 30 and the sides 26 of cart 22. An annular, preferably in the form of a planar, drum 34, is rotatably mounted within frame 28, preferably on rollers 32, or alternatively by suitable wheels or bearings. The drum rotates with respect to the frame about axis 35 of rotation that extends perpendicularly through central aperture 38 of drum 34 (and normal to the view shown in FIGS. 1 and 2). Drum 34 is typically of about 135 cm in outside diameter, and is quite thin relative to its diameter, e.g. about 1.25 cm, although these dimensions can clearly vary. Central aperture 38 preferably is dimensioned so that the body of a patient can be inserted therethrough. Preferably, drum 34 is made entirely of the same metal as frame 28, can also be solid or hollow to minimize weight, has a substantially uniform cross-sectioned configuration and mass throughout, and is radially symmetrical, substantially all thermally induced volumetric changes in the drum will be isotropic within the mean plane of the drum. To insure that the grain or crystal structure of the drum is relatively uniform, it is preferred that the drum be made by precision casting as a single unit, annealing and finish machining. It will be seen that when the configuration of the outer periphery of drum 34 is circular, the drum is mounted concentrically with frame 28 within the inner periphery of the latter.

X-ray tube 36 is positioned on drum 34 adjacent the inner periphery of the latter so as to direct a beam of X-rays substantially along the mean plane of drum 34 across aperture 38 substantially perpendicularly to axis 35, i.e. through a center line diametrically across drum 34. Similarly, an X-ray detector system, in the form of detector array 40, is mounted on drum 34 so as to detect X-rays from source 36 after the latter have traversed aperture 38. Also mounted on drum 34 are batteries 44 (shown in both FIGS. 1, 2 and 3), the X-ray generator (cathode) 46 (shown in FIG. 1) and X-ray generator (anode) 47 (shown in FIG. 2), a slice collimator 48 (shown in FIG. 2), a data acquisition system 49 (shown in FIG. 2), disk control assembly 50 (shown in FIG. 2) and power control assembly 51 (shown in FIG. 1). Batteries 44, preferably provide a high voltage supply adapted to provide the necessary peak voltage to the source to power the X-ray source during at least one scan. The batteries are provided with suitable input means for connecting the batteries to an electrical power source exterior to the gantry so that the batteries can be charged. The batteries are used to power the components secured to the drum. The data acquisition system in use preferably preprocesses and transmits the output of the array 40, preferably by a wireless rf link, to a computer (not shown) preferably positioned exterior to the gantry.

Although, of necessity, X-ray tube 36 and detector array 40 are positioned on diametrically opposite sides of drum 34, the respective masses of X-ray tube 36 and detector array 40 are the same only by rare fortuity, and typically exhibit substantially different volumetric distributions. Similarly, the battery packs 44 respectively powering X-ray source 36 and detector array 40 would only coincidentally have the same masses and volumes. Because of the disparity in mass and volume of the various components mounted on drum 34 the present invention arranges for the distribution of those components and compensating masses to insure that drum 34 is balanced for rotation about axis 35 of rotation, with the axis of the moment of inertia of mass being coaxial, and the center of thermal expansion of the assembled drum being coincident with the intersection of the mean plane of the drum 34 and the axis 35.

To this end, depending on weight and configuration, the various components are initially mounted on drum 34 with both radial symmetry and axial symmetry of the masses thereof. For example, X-ray tube 36, positioned on drum 34 as heretofore described, can be expected to have a substantial volume and dimensions somewhat larger than the thickness of drum 34. To the extent therefore that portions of source 36, when mounted on drum 34, extend transversely beyond the fiat surfaces of the latter, the weight of those portions impose a moment on the drum tending to move the latter transversely to its plane. Thus, as best shown in FIG. 3, tube 36 is positioned so that its weight is distributed equally to both fiat sides of drum 34, i.e. along a line 61 parallel to axis of rotation 35 so that its center of mass is disposed as closely as possible in the mean plane of the drum, shown as 60 in FIG. 3. As seen in FIGS. 1 and 2, X-ray detector array 40 is mounted on drum 34 on the opposite edge of aperture 38, being comparatively narrow relative to the thickness of drum 34 (so that it cannot be seen in FIG. 3), and also can be distributed so that its center of mass is also centered in plane 60. In similar manner, the remaining components including batteries 44, the cathode 46 and anode 47 of the X-ray generator, slice collimator 48, data acquisition system 49, disk control assembly 50, and power control assembly 51, and associated cabling, are all disposed so that the center of mass of each lies as closely as possible in the plane 60 of FIG. 3. The components are distributed at select radial positions about drum 34 and also so as to distribute the masses thereof as equally or symmetrically as possible both radially and axially about drum 34, such that the entire mass of the drum and its components is centered as close as possible to the intersection of axis 35 with plane 60 (seen best in FIG. 3).

To aid in the proper distribution of the masses of the various components, after they have been initially mounted on drum 34, as shown in FIG. 4, stress or torque measuring, means 62, such as a spring-scale, strain gauge, Bourdon tube or the like is attached to one of pivots 30 to measure torsion occasioned by rotation of gantry 20 transmitted to the connected pivot 30. Initially, drum 34 is positioned in frame 28 with, for example, X-ray tube 36 at top dead center and the frame positioned, with respect to cart 22 in a vertical plane as shown in FIG. 3. Frame 28 is then rotated about pivots 30 to a position between about 15° to 80°, preferably about 30°, to one side of the vertical plane as shown in full lines in FIG. 4, and a reading of any torsion then placed on pivot 30 by the frame and associated drum is made by torque-measuring means 62. The frame is then restored to its vertical position and is then rotated in the opposite direction approximately the same number of degrees as shown in dotted lines in FIG. 4, and a second measurement of the torsion is made. One of the readings is subtracted from the other and the difference thereof is halved to provide a measure or error indication of the axial mass imbalance of drum 34 and the components assembled thereon. Such measure assumes that frame 28, as above-noted, has a substantially uniform cross-section configuration and mass throughout and thus contributes nothing to any mechanical imbalance of the drum. Because the difference, if any, thus computed has both magnitude and direction, it can readily be compensated by providing means for exerting an appropriate moment to drum 34 as by adding a suitable counter weight (not shown) at a position on that surface of the drum which will result in a difference of zero when the measurements are repeated.

After the assembly of drum 34 and components has been adjusted as thus described for axial unbalance, although not shown explicitly in the figures drum 34 is rotated so that the X-ray tube is positioned sequentially, for example, at 90° to the right of top dead center, at 90° to the left of top dead center, and at 180° to top dead center, with the frame in a vertical plane with respect to cart 22 in each case. For each of these positions, the procedure for moving the frame as above described is then repeated and measurements are taken of the torsion acting on pivot 30 with the frame swung to, for example, 30° to the right and left of vertical, and from such measurements respective differences are noted. In each case, the difference can be adjusted by adding or subtracting counter weights with respect to radial positions on the drum. It will be appreciated that the procedures thus described essentially permit compensation of the mass imbalance of the drum and frame in three-dimensions. However, because of the predetermined distribution of all of the components mounted on the drum, the need and the size of such counterweights will be minimized.

For determining dynamic balance, the frame is placed in a vertical position (as shown in FIG. 3) and the drum is rotated continuously, readings being taken continuously to determine if a periodic signal will occur on the torque-measuring means 62 (seen in FIG. 4). From the magnitude and phase of such periodic signal relative to the Z-axis through the drum (e.g. when X-ray source 36 is at top dead center), one can readily determine where and how much correction mass is required to achieve dynamic balance.

As noted, thermal imbalance is substantially precluded by making both frame 28 and drum 34 of FIGS. 1–4 entirely of materials having substantially the same coefficient of thermal expansion, each having substantially uniform cross-sectional configurations and mass throughout so that any thermally induced volumetric changes are substantially isotropic. Thermal imbalances can be tested for by attaching small mirrors (not shown) at angular intervals around the periphery of drum 34 and frame 28, and directing onto such mirrors at an angle, e.g. 45°, a focussed light beam such as a laser beam. Power is then applied to the components of the drum assembly to duplicate heat generation during clinical operation. Alternatively, a drum 34 without components assembled thereon can be packed with heat-generating resistor bundles to simulate component heat generation. Any changes in dimension of the drum or frame due to thermal effects will produce a displacement of the reflected beam which can be measured readily, as by a ruled scale. The magnitude of that displacement depends on the angle of reflection and the distance of the scale from the mirror, hence in effect producing substantial amplification of the thermally induced change in dimension.

When testing indicates that substantially all differences have been compensated, it will be seen that drum 34 will be balanced for rotation about axis of rotation 35, so that the center of rotation is coaxial with the axis of the moment of inertia of mass, and the center of mass and the center of thermal expansion of the assembled drum are all coincident with the point of intersection of the axis 35 and the plane 60 (as best seen in FIGS. 1–3).

It should be appreciated that while the detailed description has been with reference to a third generation machine, the principles of the present invention apply to other CAT scanner designs including fourth generation machines.

The present invention therefore minimizes the weight and volume of the drum and its components and reduces the problems inherent in the massive, heavy and poorly mobile prior art systems without jeopardizing the precision at which the system accurately scans during drum rotation.

Since certain changes may be made in the above apparatus without departing from the scope of the invention herein involved, it is intended that all matter contained in the above description or shown in the accompanying drawings shall be interpreted in an illustrative and not in a limiting sense.

What is claimed is:

1. In an improved X-ray tomography system comprising:
   (a) an annulus including a central aperture for receiving an object to be scanned;
   (b) means for rotating said annulus about an axis of rotation; and
   (c) a plurality of components, supported by and rotatable with said annulus, for use in performing a tomographic scan;
   wherein the improvement comprises:
   said components being fixedly mounted on said annulus so as to be substantially balanced for rotation with said annulus about said axis, and so that the center of the mass moment of inertia, the center of rotation and the center of thermal expansion of said annulus and said components are substantially coincident with said axis.

2. An improved X-ray tomography system as defined in claim 1, wherein said annulus defines a mean plane normal to said axis of rotation, and at least some of said components each has a center of mass disposed in said mean plane.

3. An improved X-ray tomography system as defined in claim 1, wherein said means for rotatably supporting said annulus includes a frame, wherein said frame is formed of a light-weight, rigid, material and has a substantially uniform cross-section configuration and mass throughout.

4. An improved X-ray tomography system as defined in claim 3, wherein said annulus is formed of a light-weight, rigid, material and has a substantially uniform cross-section configuration and mass throughout.

5. An improved X-ray tomography system as defined in claim 4, wherein said annulus and frame are made of materials having substantially the same coefficient of thermal expansion.

6. An improved X-ray tomography system as claimed in claim 5, wherein substantially all thermally induced volumetric changes in said frame and annulus are isotropic.

7. An improved X-ray tomography system as defined in claim 1, including:
   a cart having a pair of supporting arms, said frame being pivotally mounted about pivot means between said arms along a diameter of said frame passing though said center of rotation;
   load-measuring means for measuring torsion occasioned by rotation of said frame about said pivot means.

8. An improved X-ray tomography system as defined in claim 1, wherein said components are mounted on said annulus to preserve mass radial symmetry and mass axial symmetry of the latter.

9. In a tomography system comprising a plurality of components, including an X-ray source, for performing a tomographic scan, and support means for supporting an annulus rotatable in its mean plane, said components being mounted on said annulus for rotation in said plane about an axis of rotation extending through the central aperture of said annulus such that X-rays projected along said plane from said source through a plurality of angular positions about said axis may pass through an object located within said annulus,
   a method of balancing said annulus about said axis so that the center of rotation, the center of mass, the mass moment of inertia and the center of thermal expansion of said annulus are substantially coincident with said axis of rotation.

10. The method of balancing as defined in claim 9, including the step of mounting said components on said annulus so as to preserve mass radial symmetry and mass axial symmetry of said annulus.

11. The method of balancing as defined in claim 9 including the steps of rotating, with said annulus disposed in one of a plurality of different rotational orientations within said frame, said frame and annulus supported therein about a pivotal axis parallel to the plane of said annulus to first and second predetermined angular positions in opposite directions from vertical orientation of said frame and annulus;

measuring the torsion created about said pivotal axis at each of said first and second positions;

determining the difference between each measurement of torsion at each of said first and second positions, and halving said difference to obtain an error determination; and so positioning on said annulus a mass of magnitude as to reduce said error determination to substantially zero upon repetition of said rotating and measuring steps.

12. The method of balancing as defined in claim 11, further including the steps of repeating the sequence of steps of rotating, measuring, determining and positioning for each of the others of said plurality of different rotational orientations of said annulus within said frame.

13. The method of balancing as defined in claim 1, further including the steps of continuously rotating said annulus about said axis of rotation and continuously measuring any changes in torque produced during said continuous rotating.

* * * * *